(12) United States Patent
Nakao

(10) Patent No.: US 7,833,238 B2
(45) Date of Patent: Nov. 16, 2010

(54) ENDOSCOPIC ANCHORING DEVICE AND ASSOCIATED METHOD

(75) Inventor: Naomi L. Nakao, New York, NY (US)

(73) Assignee: Granit Medical Innovations, LLC, New York, NY (US)

( * ) Notice: Subject to any disclaimer, the term of this patent is extended or adjusted under 35 U.S.C. 154(b) by 746 days.

(21) Appl. No.: 11/109,004

(22) Filed: Apr. 19, 2005

(65) Prior Publication Data

US 2005/0234512 A1 Oct. 20, 2005

Related U.S. Application Data

(60) Provisional application No. 60/563,534, filed on Apr. 19, 2004.

(51) Int. Cl.
  *A61B 17/08* (2006.01)
  *A61B 17/04* (2006.01)
  *A61D 1/00* (2006.01)

(52) U.S. Cl. .................. 606/151; 606/219; 606/232

(58) Field of Classification Search ............. 606/232, 606/151, 75, 213, 216, 219, 220, 233, 326, 606/327, 330; 607/126, 128, 130; 227/902; 411/448, 456, 459, 460, 466, 467, 483
See application file for complete search history.

(56) References Cited

U.S. PATENT DOCUMENTS

| | | | |
|---|---|---|---|
| 643,003 A | 2/1900 | Pollock | |
| 943,263 A | 12/1909 | Moraneck | |
| 1,510,416 A | 9/1924 | Pietz et al. | |
| 2,113,246 A | 4/1938 | Wappler | |
| 2,968,041 A | 1/1961 | Skold | |
| 3,378,010 A | 4/1968 | Codling et al. | |
| 3,518,993 A | 7/1970 | Blake | |
| 3,882,854 A | 5/1975 | Hulka et al. | |
| 3,958,576 A | 5/1976 | Komiya | |
| 4,038,987 A | 8/1977 | Komiya | |
| 4,367,746 A | 1/1983 | Derechinsky | |
| 4,394,864 A | 7/1983 | Sandhaus | |
| 4,446,865 A | 5/1984 | Jewusiak | |
| 4,485,817 A | 12/1984 | Swiggett | |
| 4,496,090 A | 1/1985 | Crevier et al. | |
| 4,681,107 A | 7/1987 | Kees, Jr. | |
| 4,706,668 A | 11/1987 | Backer | |
| 4,714,075 A | 12/1987 | Krauter et al. | |
| 4,735,194 A | 4/1988 | Stiegmann | |
| 4,759,364 A | 7/1988 | Boebel | |
| 4,796,627 A | 1/1989 | Tucker | |
| 4,821,721 A | 4/1989 | Chin et al. | |
| 4,841,888 A | 6/1989 | Mills et al. | |

(Continued)

*Primary Examiner*—Todd E Manahan
*Assistant Examiner*—Lindsey Bachman
(74) *Attorney, Agent, or Firm*—R. Neil Sudol; Henry D. Coleman; William J. Sapone

(57) ABSTRACT

An endoscopic fastening assembly having a diameter sufficiently small so that the fastening assembly is slidably insertable into a working channel of a flexible or rigid endoscope for performing a fastening operation, comprises one or more surgical anchors within an elongated tubular member configured for delivery and deployment of said anchors. One or more anchors being disposed in a substantially closed pre-deployment configuration inside the tubular body are configured for being delivered and deployed into a target tissue while remaining in a substantially closed configuration, and assuming its open anchoring properties only once embedded in tissue.

9 Claims, 15 Drawing Sheets

U.S. PATENT DOCUMENTS

| | | |
|---|---|---|
| 4,880,015 A | 11/1989 | Nierman |
| 4,887,612 A | 12/1989 | Esser et al. |
| 4,934,364 A | 6/1990 | Green |
| 4,945,920 A | 8/1990 | Clossick |
| 4,971,067 A | 11/1990 | Bolduc et al. |
| 4,983,176 A | 1/1991 | Cushman et al. |
| 5,015,249 A | 5/1991 | Nakao et al. |
| 5,022,126 A | 6/1991 | Davis |
| 5,032,127 A | 7/1991 | Frazee et al. |
| 5,049,153 A | 9/1991 | Nakao et al. |
| 5,156,609 A | 10/1992 | Nakao et al. |
| 5,222,961 A | 6/1993 | Nakao et al. |
| 5,478,353 A * | 12/1995 | Yoon .......................... 606/213 |
| 5,573,543 A * | 11/1996 | Akopov et al. .............. 606/144 |
| 5,893,856 A * | 4/1999 | Jacob et al. .................. 606/151 |
| 5,961,539 A * | 10/1999 | Northrup et al. ............ 606/232 |
| 6,364,897 B1 * | 4/2002 | Bonutti ....................... 606/232 |
| 6,986,775 B2 * | 1/2006 | Morales et al. ............. 606/139 |
| 7,186,262 B2 * | 3/2007 | Saadat ........................ 606/232 |
| 2005/0075654 A1 * | 4/2005 | Kelleher ..................... 606/151 |
| 2006/0025784 A1 * | 2/2006 | Starksen et al. ............. 606/151 |

* cited by examiner

ENDOSCOPIC ANCHORING DEVICE AND ASSOCIATED METHOD

RELATED APPLICATIONS

This application claims the benefit of the priority of U.S. Provisional Application No. 60/563,534, filed on Apr. 19, 2004, which application is incorporated herein by reference in its entirety.

FIELD OF THE INVENTION

The present invention relates to an endoscopic anchoring device and surgical anchors to be used in conjunction with flexible or rigid endoscopy, or during open surgery. Anchoring is performed on internal body tissues as part of a surgical diagnostic or therapeutic procedure using one or more surgical anchors and an associated anchor delivery and deployment assembly designed for delivering one or more anchors.

BACKGROUND OF THE INVENTION

Conventional surgery often necessitates the use of clips, staples, or other surgical fasteners. Such procedures generally require that an extensive incision be made (open surgery), or that a series of small incisions be created, through which several cannulas are placed for providing access to a body cavity (laparoscopic surgery).

Currently, there is no reliable method for securing clips, staples, or other surgical fasteners inside a patient's body in conjunction with a flexible endoscope. The challenge entailed in creating a fastener and a delivery and deployment device that may be passed through a flexible endoscope is two-fold: firstly, the working channel of an endoscope is very narrow requiring a device with an outer diameter sufficiently small to pass through it. Secondly, a flexible endoscope bends along with curvatures of the internal body lumens, requiring similar flexibility of a fastener delivery and deployment device to enable such a journey. Both of these challenges have not yet been surmounted; hence there are no such devices currently available. Suturing operations have similar limitations, and as such physicians have been unable to perform surgical procedures via natural body orifices using a flexible endoscope.

When performing a procedure with an instrument passed through a flexible endoscope, the simplest method to operate this instrument is through either a pushing, or pulling motion performed proximally by the operator. As the surgical instruments traverse bends in the endoscope, a turning or torquing motion performed proximally, does not translate in a 1:1 ratio distally. Pushing or pulling, on the other hand is ergonomically simpler for the operator, and is transmitted through the entire instrument better. Therefore, most operations performed through the flexible endoscope, such as biopsy, or polypectomy, employ a push or a pull action at the handle, or proximal aspect of the instrument. It would therefore be advantageous to provide a device that would enable application of fasteners through a simple push of the extracorporeal, proximal aspect of the fastener application device.

Laparoscopic surgery has been developing rapidly in the past few years because it is less invasive than open surgery. These procedures enable sewing or stapling tissue via a series of small abdominal incisions through which a number of cannulas are placed. Rigid instruments are passed through these cannulas and manipulated from outside the body. The surgical procedure is visualized with a camera, which is introduced through a separate cannula.

Providing smaller diameter instruments capable of reaching surgical sites through smaller access ports or cannulas would provide an advantage during laparoscopic surgery because smaller incisions cause a lesser injury, providing for a more rapid healing process. The size of the instruments used to deliver surgical staples, for example, is dictated by staple size.

The currently used staple delivery device sizes have been decreased by designing the device for delivery of a closed staple. This enables passage of these devices through smaller diameter cannulas. Upon reaching the operative site, such a staple must be opened by some means, in order to engage a target tissue, after which the staple is again closed upon the tissue. Consequently, a staple may be displaced, or slip out of the delivery device's jaws. Furthermore, the force required to open and close the staple or clip is magnified because it is transmitted through the distance of the shaft. Providing an anchoring system, that would permit introduction and delivery of an anchor in a substantially closed configuration, would preclude a need for the "closed open closed" design.

Although there appear to be no commercial devices on the market that enable stapling through the working channel of the flexible endoscope, U.S. Pat. Nos. 5,222,961, 5,156,609, 5,015,249 and 5,049,153 to Nakao et al describe various embodiments of an endoscopic stapling device. U.S. Pat. No. 5,015,249 describes a flexible stapler whereby the staple is configured with an open bias, and releasably connected to a rod member. The staple is ejected by pushing the rod member forward. Upon engagement of the staple with tissue, the staple being opened by its open bias, a tubular member is pushed over the staple to close it. The problem with the embodiment of the '249 patent is the following: bowel wall thickness, for example, is approximately 0.5 cm, and its consistency is slightly firmer than that of a calf's liver. Closing an indwelling staple by pushing a tubular member over it may push the entire staple through the bowel wall.

U.S. Pat. No. 5,049,153 describes a flexible stapler, wherein a staple with an open bias is disposed in the prefiring position inside said stapler's open jaws. The stapler is brought to the tissue with the indwelling staple, closed upon the tissue, and once the staple locks, the staple legs are released. U.S. Pat. No. 5,156,609 describes a plurality of second staples each having a spring bias. U.S. Pat. No. 5,222,961 describes various additional means of locking a staple. All the above-mentioned patents address staples to be delivered by an endoscopic stapler. The invention disclosed herein describes an anchoring device and an instrument for delivering one or more anchors held together by a suture thread or another line element. This device assembly is designed quite differently than the staplers described above.

It is therefore desirable to provide a surgical anchor with an associated delivery and deployment assembly for applying one or more anchors, wherein the anchoring system is configured for passing through the working channel of a flexible endoscope.

It is further desirable to provide an anchoring system capable of reaching surgical sites through smaller access ports during laparoscopic surgery.

It is yet further desirable to provide an anchoring system whereby the anchor may remain in a substantially closed configuration throughout the entire fastening operation, and assumes its open configuration only when deployed into tissue.

It is also desirable to provide an anchoring system, which is ergonomically beneficial because it can be operated extracorporeally through a pushing operation.

The benefits of the present invention in addressing the drawbacks of the prior art and the objectives and needs noted above will be more readily apparent from the description and drawings of the invention set forth herein.

BRIEF DESCRIPTION OF THE INVENTION

As broadly contemplated, the endoscopic anchoring system of the invention comprises an anchoring delivery and deployment assembly and related surgical anchors to be used in conjunction with a flexible or rigid endoscope. The invention relates to an anchoring operation using one or more surgical anchors coupled with suture thread or another line element to be used for approximating internal body tissues together through a synching operation.

In one embodiment of the present invention, an endoscopic anchoring system comprises an elongate hollow or tubular body having an outer diameter sufficiently small, so as to be slidably insertable through a working channel of an endoscope. The hollow tubular body holds one or more anchors, and includes a pushing device or element to deploy the anchors, such as a rigid or flexible push rod that moves in the tubular body for pushing the anchors in the distal direction. The tubular body is provided at a distal end thereof with a sharp hollow tip, such as a hollow needle, which is coextensive with a distal end of the body and serves to pierce the target tissue for the purpose of delivering the anchors. The anchors have a collapsed state when positioned in the hollow tubular body and are operable to splay to an open state when ejected from the tubular body as further discussed herein below.

In one embodiment of the invention, the anchors include anchor spines, which are curved at their distal ends for anchoring into tissue, and are sharply pointed at their distal ends for the purpose of easily penetrating the tissue. Two corresponding spines are formed from one thin metal rod that is bent at a medial aspect thereof. Several such metal rods are thusly bent, and coupled with a crimping mechanism such as, for example, a metal ring or collar. The crimping mechanism is placed proximate the bight portion created by the bend in the rods, forming a proximal loop.

The distal spines extending from the crimping mechanism terminate with an outward curve as described above. When the spines are in their most open configuration, corresponding spines are situated at an angle of approximately 100 degrees from one another at the anchor's most splayed position, however function well even at lesser angels such as 70-80 degrees. An anchor may not be capable of opening to its maximal open position when embedded in tissue, therefore it is important that the anchor functions well even at a partially opened state. A suture thread or another line element traverses through the proximal loop of each anchor. While in the embodiment described above the loop is configured from the proximal bight portion of the spines held together by the crimping mechanism, in another embodiment the loop may be separately formed, as further described below.

The anchors are configured for engaging tissue and may be formed of a suitable material, such as metal or plastic, for example. In one embodiment the anchors are made of a shape memory alloy. Shape memory alloys (SMAs) are particularly useful for this application because of their ability to undergo a reversible transformation from an austenitic (hardened) state to a martensitic (malleable) state with a change in temperature. This transformation is sometimes referred to as thermoplastic martensitic transformation.

In the embodiment wherein the anchors are made of an SMA, the spines are formed by "backing in" their open configuration. Thus, the desired configuration of the spines when in their hardened, austenite state is an open one, whereby the angles between spines are at about 110 degrees, and the distal aspects of the spines are at their maximum curve for optimal grasping, or anchoring into tissue.

These anchor spines rely on the property of shape memory to achieve their desired effect, that is to say, they rely on the fact than when the SMA spines are cooled to its martensitic (malleable) state, the anchor will be subsequently deformed and will retain its new shape, such as when stored inside the hollow tubular body, or the needle; but when it is warmed to its austenitic (hardened or firm) state, for example when released inside body tissue thereby being exposed to body temperature, the original shape (i.e., splayed in an open state) will be at least partially recovered, as discussed above.

In another embodiment, a crimping mechanism is used to hold the spines together, and may be formed of a different or similar material as the spines. The anchors are contained within the elongated tubular body that acts as an anchor delivery tube and terminates in a needle. The anchors are stacked behind each other inside the elongated tubular body, and are pushed forward by the pushing device that acts on the rearmost anchor's proximal end. As the rearmost anchor is pushed, in turn, it pushes the next anchor and so on until all of the anchors are deployed out of the distal end of the device.

Surgery for morbid obesity (bariatric surgery), which is being performed with much greater frequency, also requires either an open or laparoscopic technique. These patients are particularly risky because of their co-morbidities, and the surgery takes hours with all the risks of prolonged anesthesia, and organ failure. A particular method of employing the anchoring device is described below, wherein a rather low risk endoscopic procedure is performed. This procedure results in a gastric restrictive operation, which may supplement, or precede the more invasive operation of small intestinal bypass surgery.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the Figures.

DETAILED DESCRIPTION OF EMBODIMENTS OF THE INVENTION

Definitions

The term "endoscopic" is used herein to designate any of a variety of minimally invasive surgical procedures wherein optical elements are used to view internal spaces and tissues of a patient through relatively small surgically created openings or natural orifices. Concomitantly, the term "endoscope" as used herein refers to any optical or tubular instrument inserted through such openings or orifices for purposes of enabling visualization of and/or access to internal tissues during a minimally invasive procedure.

During a laparoscopic procedure, for example, an optical element may be inserted through one small incision, while one or more cannulas would be inserted through one or more separate incisions. The surgical instruments inserted through the cannulas are visualized by means of the first optical element. During a flexible endoscopic procedure on the other hand, a flexible endoscope may include, for example, both the optical element and one or more channels through which the surgical instruments are passed.

Figure 1:
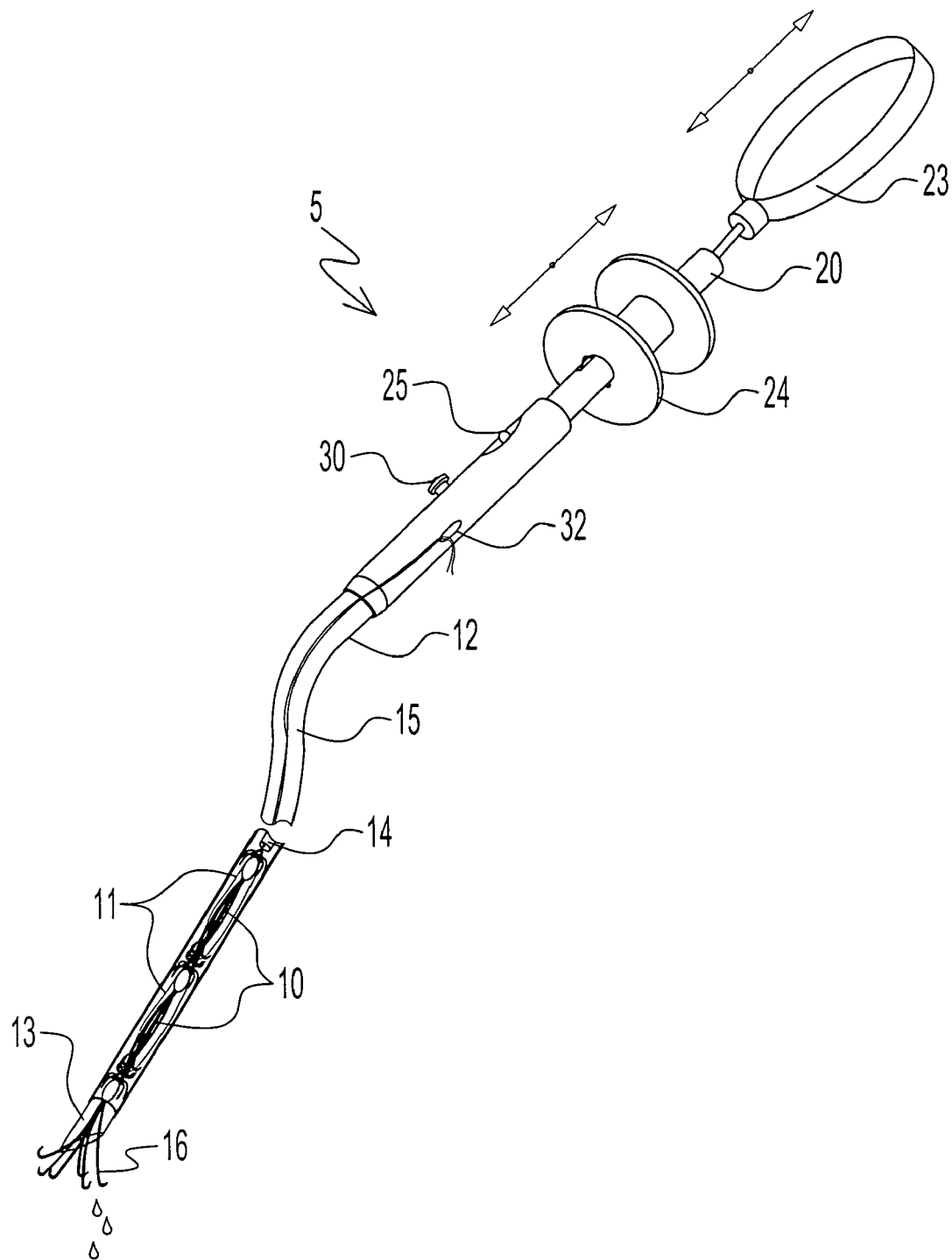
FIG. 1 is a perspective view of an embodiment of the present invention.

FIG. 1 is a perspective view of an endoscopic fastening assembly 5 in accordance with an embodiment of the invention. The fastening assembly 5 includes a plurality of anchors 10 attached to a thread or line element 11, and is configured to secure tissue that is internal to the body using a flexible or rigid endoscope. As such fastening assembly 5 is configured and operable to be manipulated within an endoscope during flexible endoscopy or a cannula during a laparoscopic procedure. Fastening assembly 5 includes an elongated hollow or tubular body 12 that holds a plurality of anchors 10 and an elongated pushing device to deploy the anchors, such as a pushing device 14 that moves or slides in body 12 for pushing anchors 10 distally for their deployment into tissue. The tubular body 12 is preferably flexible for being passed through and manipulated in a flexible endoscope, and terminates at said tubular body's distal end with a sharp hollow tip or hollow needle 13.

The anchors are configured for engaging tissue and may be formed of a suitable material, such as metal or plastic, for example. The anchors are preferably small enough to be deployed directly into the target tissue. In one example, the invention is used in the intestine and for that purpose the anchors must be small enough to be deployed into a patient's intestinal wall, which is approximately 0.5 cm thick.

In one embodiment, the anchors include spines and a crimping mechanism, wherein the spines are made of a shape memory alloy (SMA) such as Nitinol (NiTi). When the spines are formed from an SMA, they are deformed from their original "backed in" configuration, which is the open, splayed state of the anchor, to a new configuration such as a collapsed anchor state when cooled below the temperature at which the alloy is transformed from the austenitic to the martensitic state.

The temperature at which this transformation begins is usually referred to as Ms, and the temperature at which it finishes is Mf wherein M stands for martensite, s stands for start, and f stands for finish. When the spines thus deformed are warmed to a temperature at which the alloy starts to revert back to austenite, referred to as Af (Af being the temperature at which the reversion is complete), the deformed spines will begin to return to their original configuration, such as the splayed or open state.

In addition to the temperature dependence of SMA, certain shape memory alloys also display stress-induced martensite (SIM). When stress is applied to the alloy, it deforms elastically. At a critical stress, the austenitic alloy begins to transform to stress-induced martensite. This transformation takes place at essentially constant stress until the alloy becomes fully martensitic. From that point on, when further stress is applied, the martensite yields first elastically and then plastically.

When the stress is released, the martensite recovers elastically to a point at which there is zero residual stress, but a non-zero residual strain. Because the alloy is below As, the deformation is not recoverable until heating above As results in conversion to austenite. At that point, if the sample is unrestrained, or only minimally restrained such as the anchor inside tissue, the original shape baked into the anchor will prevail.

Certain Nitinol (NiTi) SMAs display stress-induced martensite at temperatures near mammalian body temperatures (35 to 40 degrees Celsius). For the invention, one can select any SMA, and test for the existence of the SIM effect at a desired temperature. In the example of one anchor embodiment made of the NiTi SMA, the SIM effect is displayed as follows: When the anchor 10 is stress stored inside the tubular body or needle 13, or even inside a stiffly flexible catheter or tubular body, it is in a stress induced martensite stage. When it is released while being embedded into tissue (body temperature being above As of the particular NiTi alloy, it transforms back into the austenite stage, with the anchor returning to its original splayed or open configuration, with hooked spines for optimal anchoring action in the target tissue.

One embodiment of an anchor includes a bullet or oval shaped connector body 34 that includes a plurality of hooked legs 16 in the form of wires or spines, which are coupled to the body. Alternatively, the anchor may be in the form of a plurality of hooked legs, wires or spines that are held together at a connection location with a crimping mechanism 54. The hooked legs 16 project from the connector body or structure such that when the respective anchor is in a collapsed pre-deployment state, the hooked legs 16 are substantially parallel to one another on a common side of the connector body or structure. The hooked legs have ends away from the connector body or structure that are curved or blunt on a side facing away from the connector body or structure. Concomitantly, the distal side of the anchor is curved or blunt facing in a distal direction, away from the connector structure. The anchor spines 16 are configured and operable to splay out to at least a partially open state when deployed into a target tissue.

Figure 6:
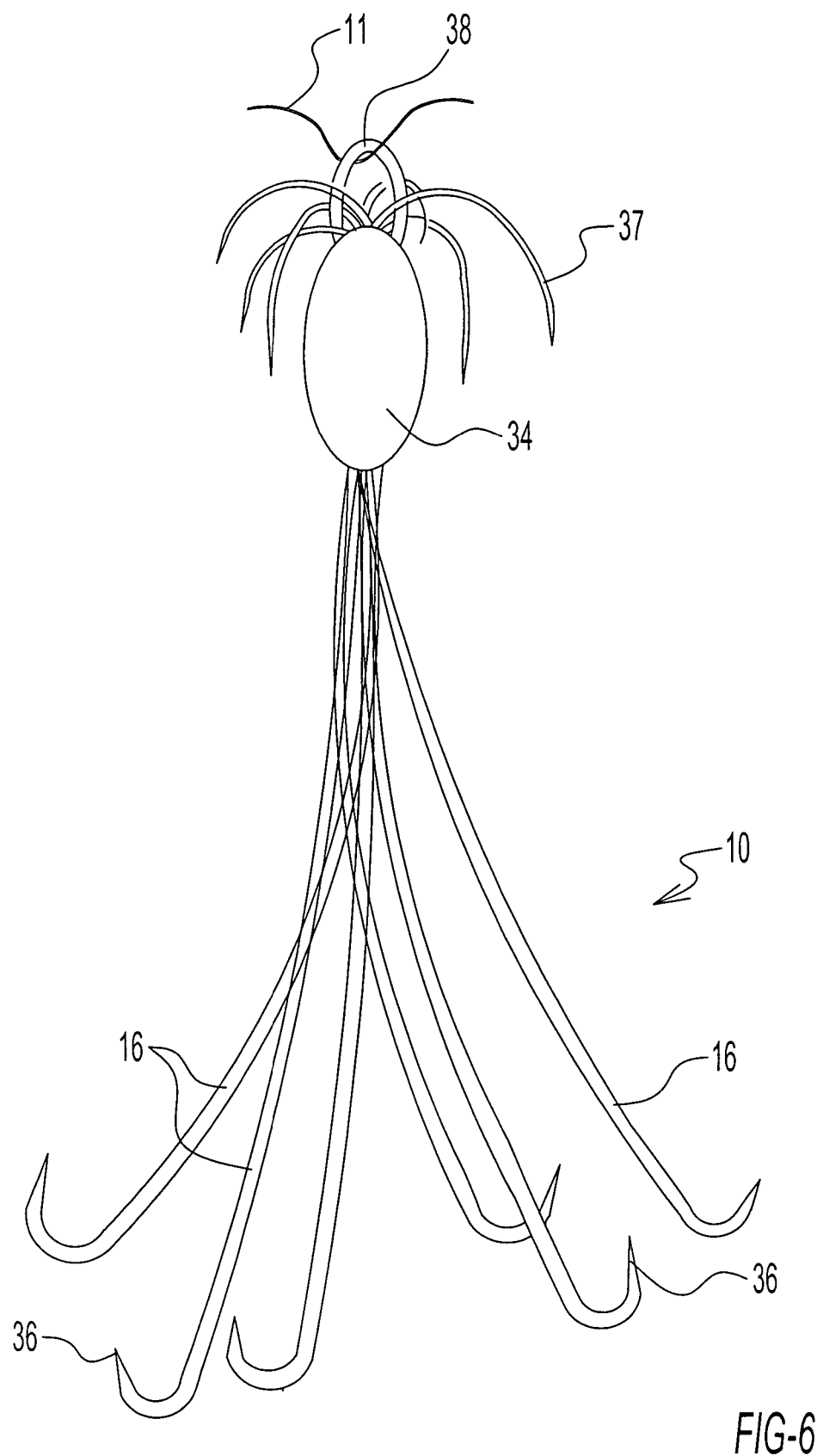
FIG. 6 is a perspective view of a full open anchor in accordance with an embodiment of the invention.
Figure 7:
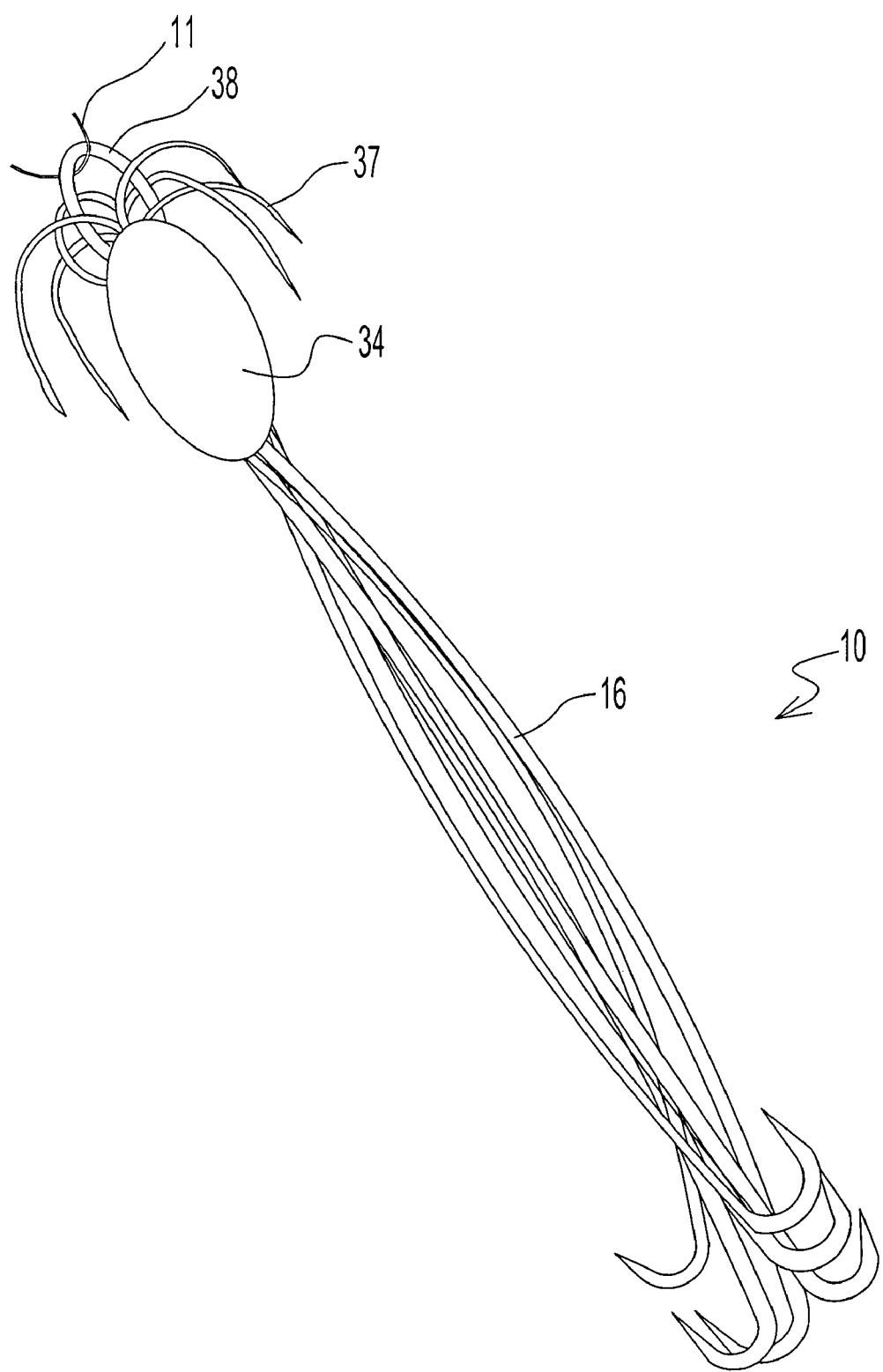
FIG. 7 is a perspective view of an anchor as in FIG. 6 in a collapsed state and held together by a crimping mechanism.

The spines 16 include curved and sharp distal ends 36 for grasping tissue and preventing migration of the anchor in the tissue as shown in FIGS. 6 and 7. In one embodiment, the spines 16 might also include curved proximal ends 37 for further grasping tissue (FIGS. 6 and 7). In another embodiment, the anchor is elastic and is configured to splay to an open state under a spring bias force. For example, the anchor spines may be stainless steel.

Whether the spines are made of a shape memory alloy or an elastic spring bias material, the anchor body or crimping mechanism may be made of the same or different material as the spines.

Figure 2:
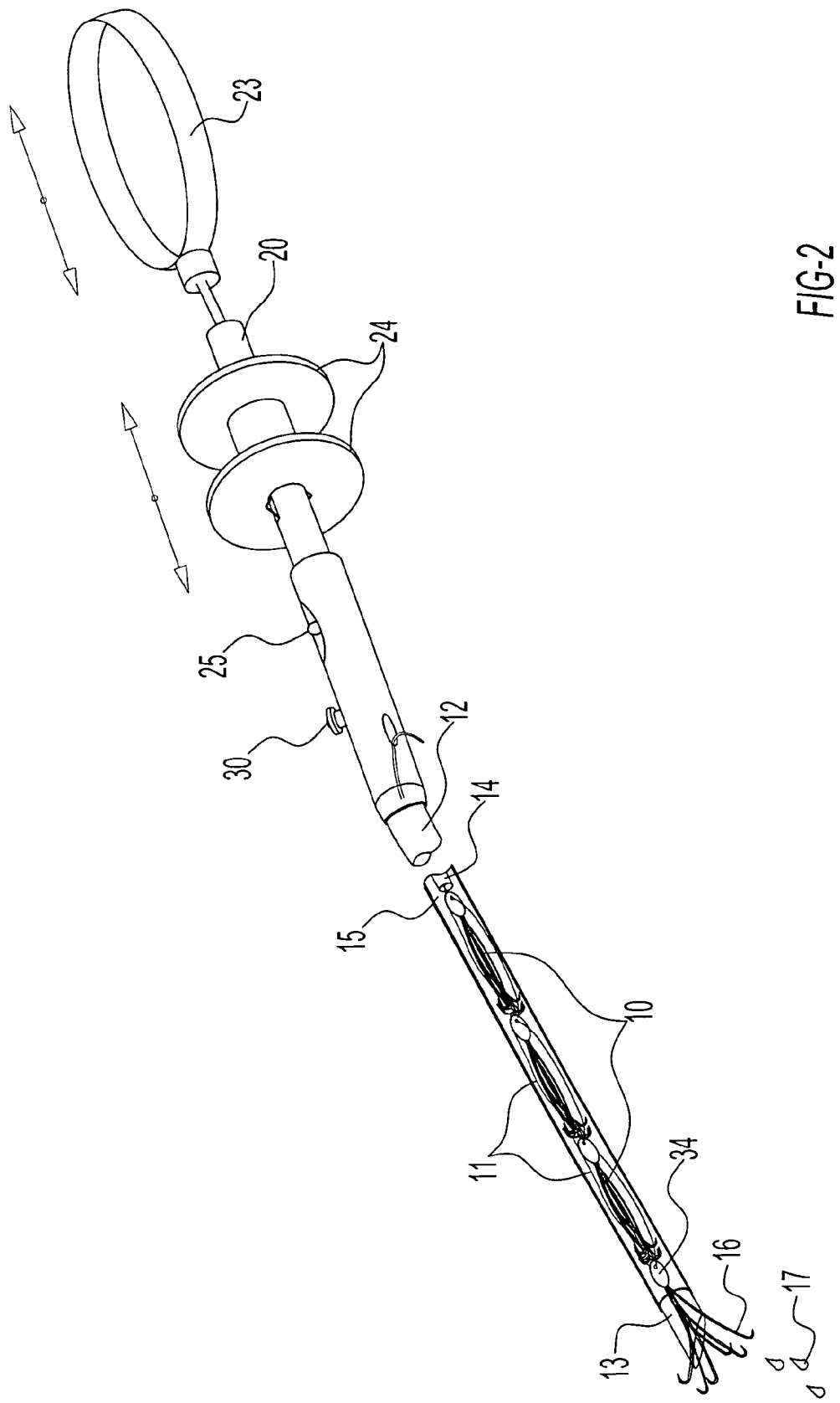
FIG. 2 is another perspective view of an embodiment of the present invention.

Tubular body 12 terminates in a sharp tip or hollow needle 13 configured to pierce and enter a target tissue as shown in FIGS. 1 and 2. The anchors are deployed out of the end of needle 13.

The expandable anchors 10 are contained in a collapsed state within tubular body or catheter 12. In one embodiment, body 12 includes a fluid passageway 15 to conduct hot fluid to induce an austenitic state, namely the splaying of the spines and the curvature of the individual spines 16 of the anchors 10. The same embodiment may be used to conduct cold fluid to induce the malleable, martensitic state if necessary.

The assembly 5 includes an actuation mechanism or handle 20 that is provided with a thumb ring 23 and finger ring 24, used to move the pushing device 14 for the purpose of deploying anchors 10. Actuation mechanism 20 includes an indexing locking mechanism 25 for positive stops of the push rod and for individual deployment of each anchor.

Figure 4:
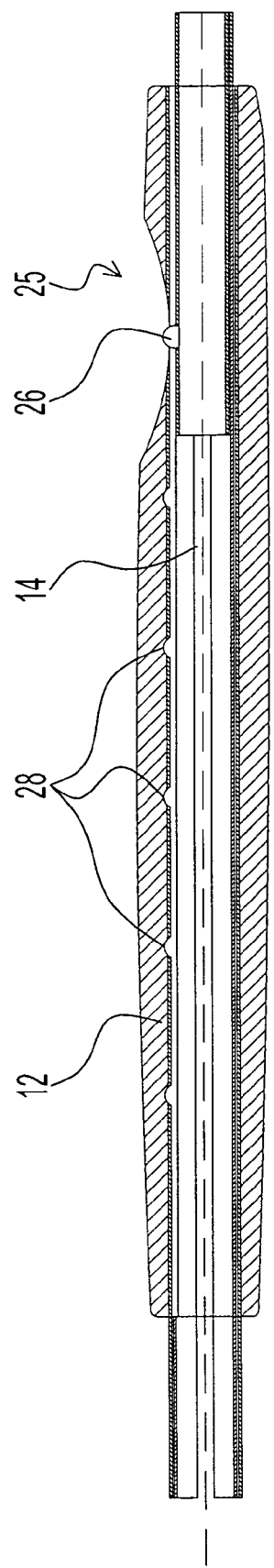
FIG. 4 is a cross sectional view of a portion of an embodiment of the invention showing a locking mechanism.
Figure 5:
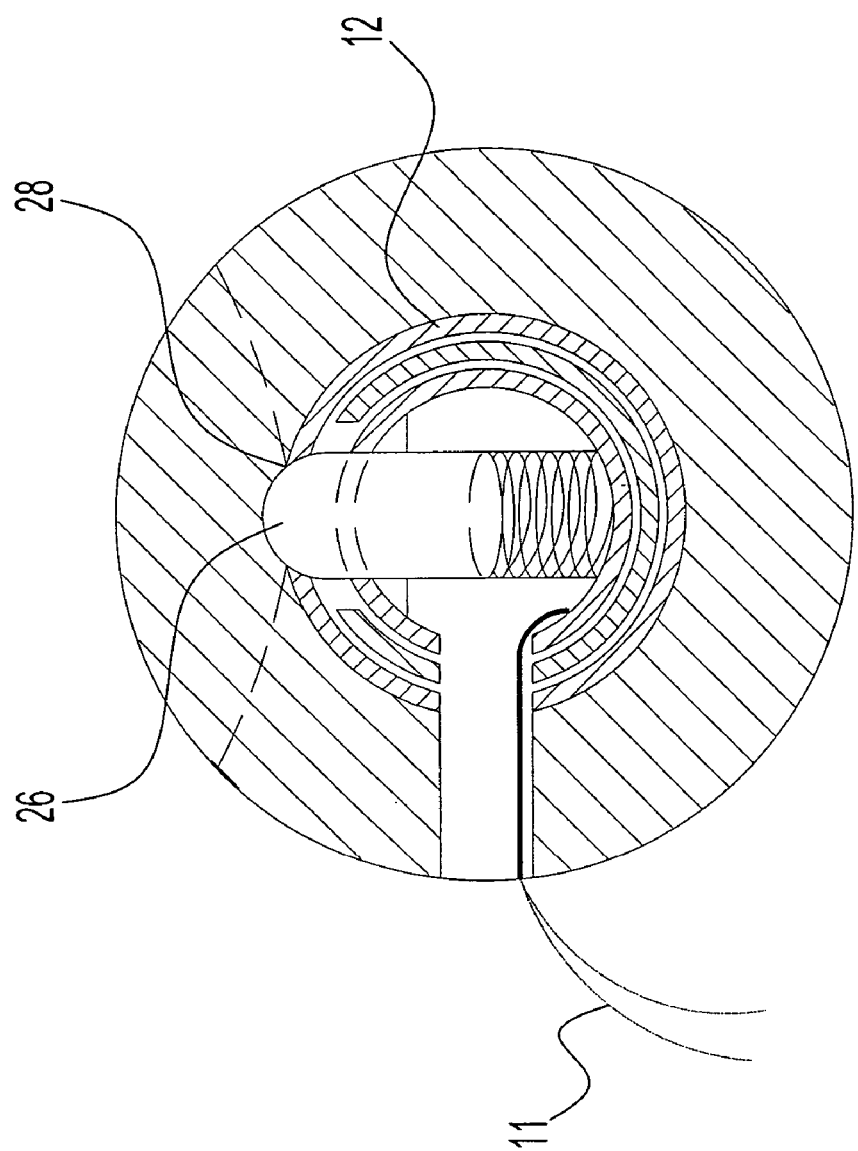
FIG. 5 is a cross sectional view of the portion of FIG. 4 showing a ball catch of the locking mechanism.

FIG. 4 illustrates an embodiment of the locking mechanism for pushing device 14 wherein a spring-loaded ball catch 26 (see FIG. 5) engages a series of indents 28 formed in elongated hollow tubular body 12. Device 5 also includes a fluid injection port 30 for introducing fluid 17 toward the passageway 15 and a thread-port 32 for introducing thread, or line element 11. FIG. 2 shows another perspective of device 5.

Referring to FIG. 2, the cutaway sectional view of the distal end of device 15 illustrates anchor spines 16 emerging from the end of the elongated body 12 and splaying out to an open configuration for anchoring tissue. As illustrated in FIG. 6, the spines 16 have sharp, curved ends 36, for respectively piercing, penetrating and anchoring tissue as noted below. A crimping mechanism 34 forms a body that holds the individual spines 16 together.

Figure 10:
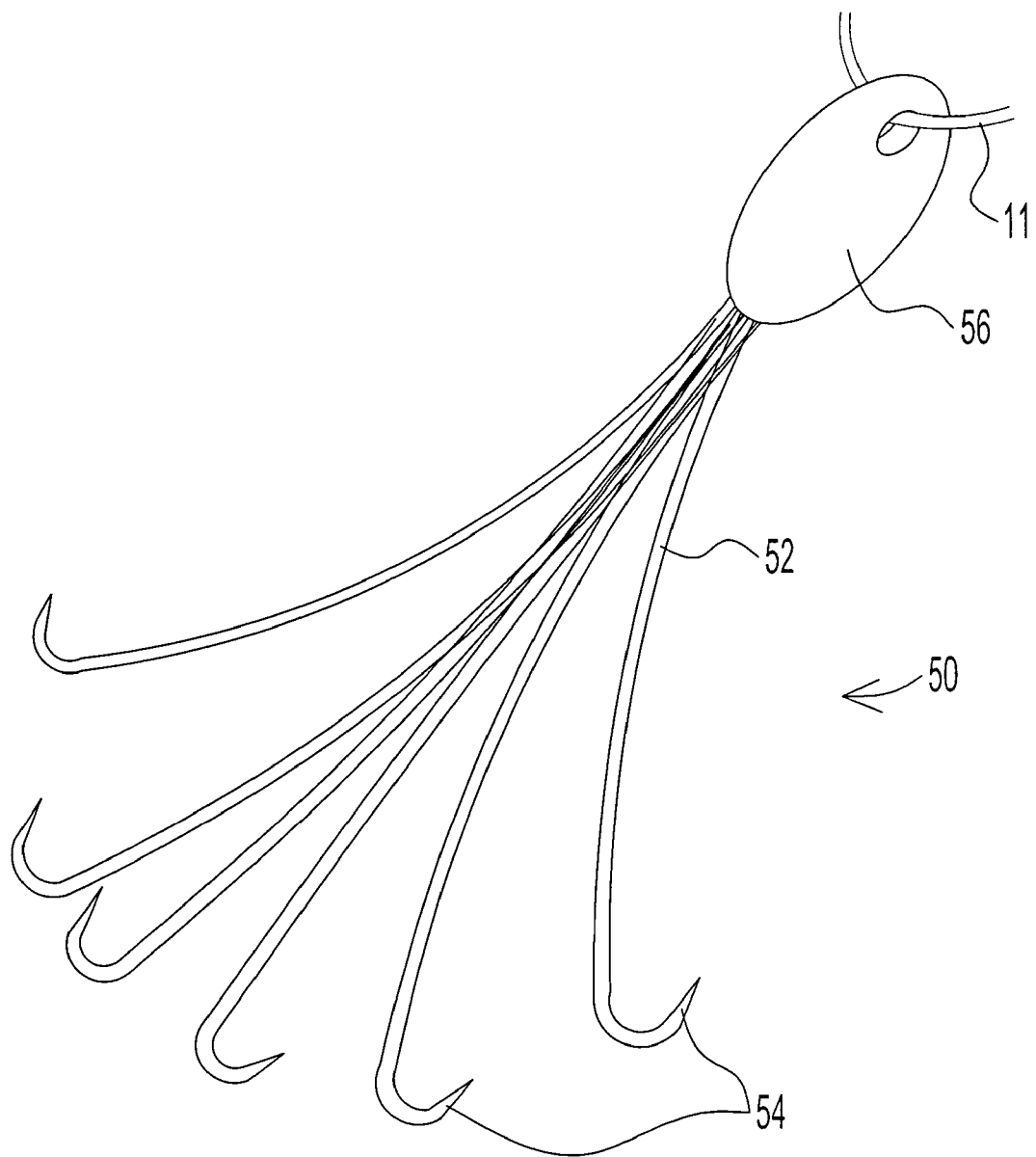
FIG. 10 is a perspective view of a full open alternative anchor in accordance with an embodiment of the invention.
Figure 11:
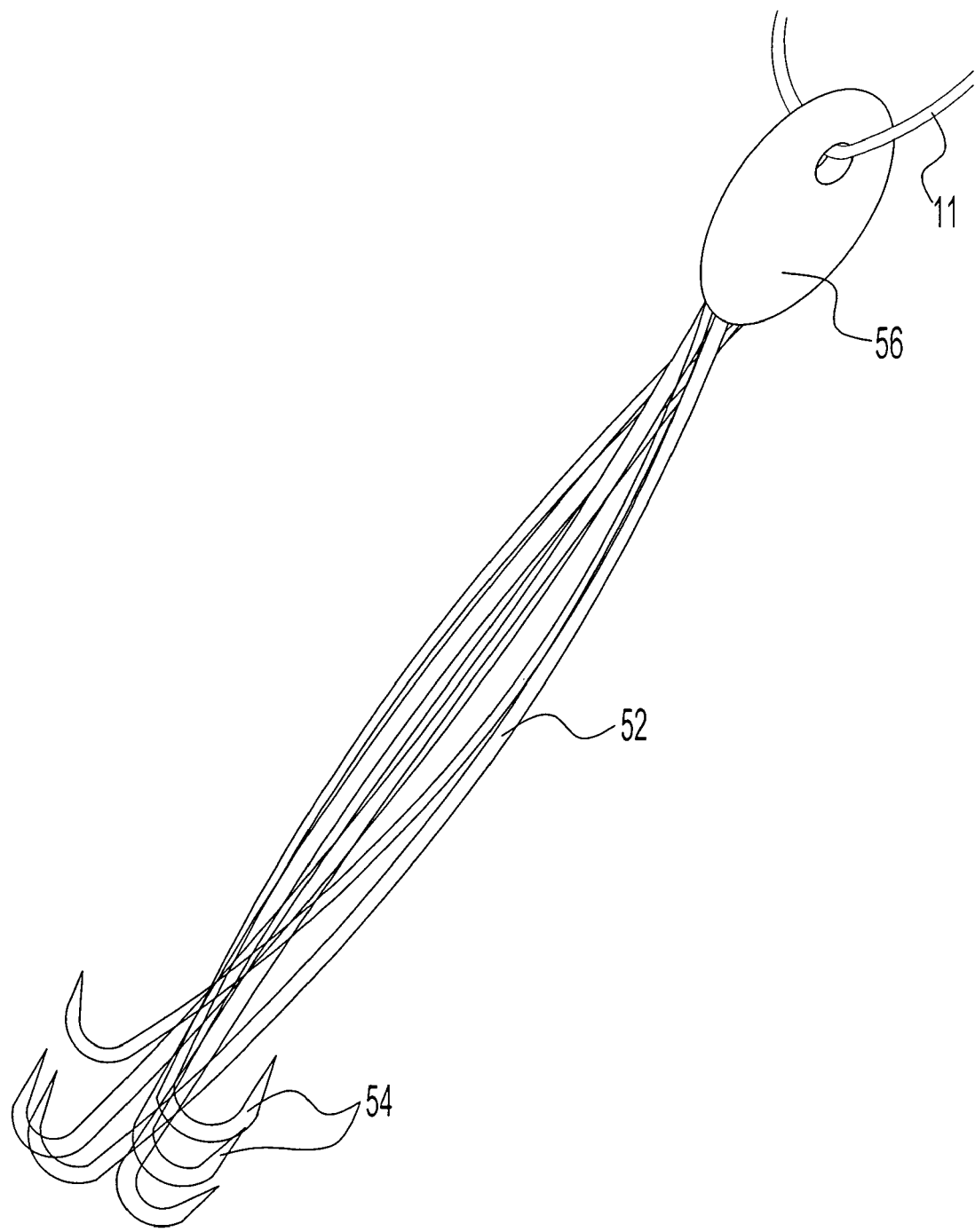
FIG. 11 is a perspective view of an anchor as in FIG. 10 in a collapsed state.
Figure 14:
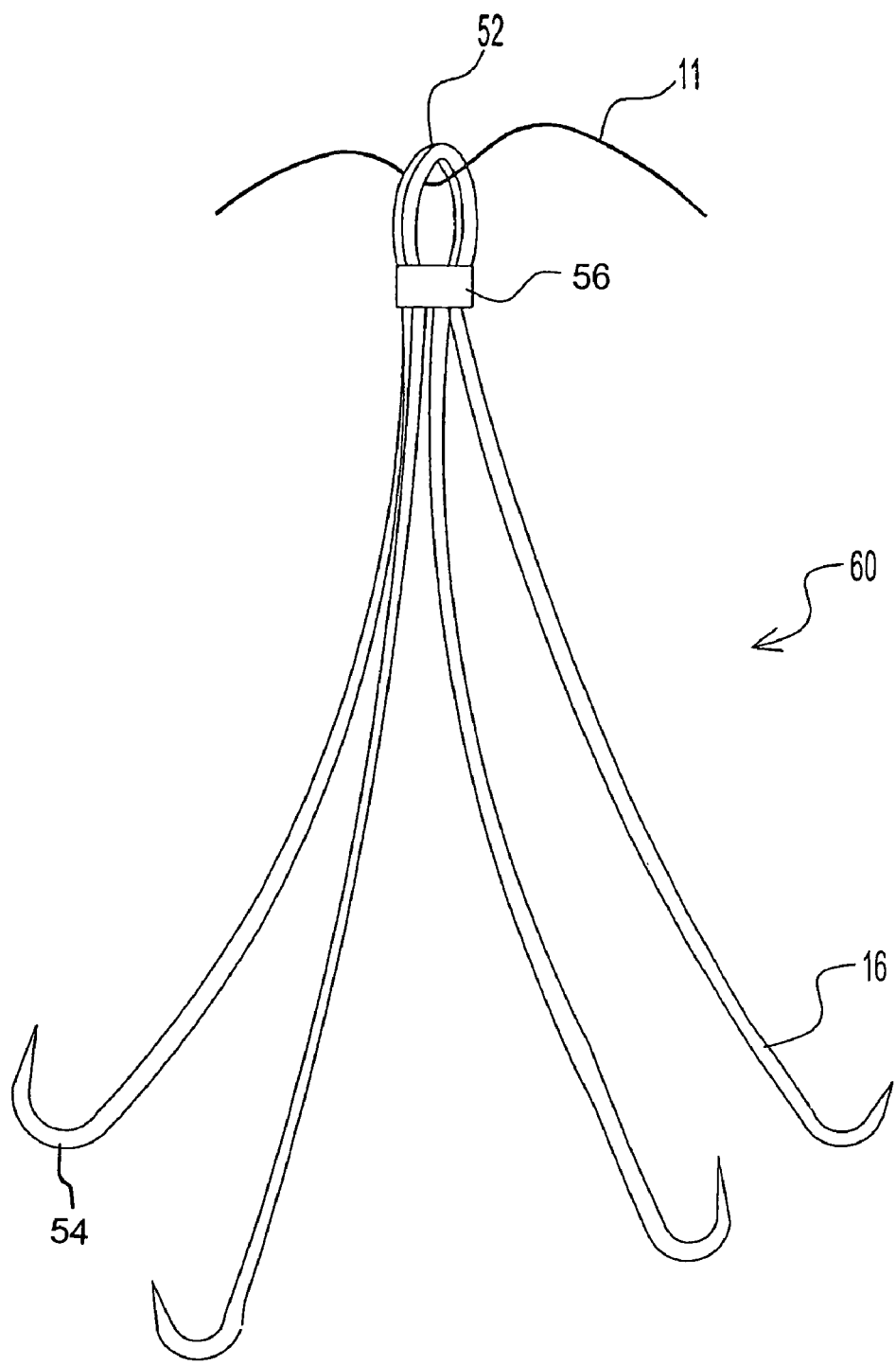
FIG. 14 is a perspective view of another embodiment of an anchor in an open configuration.

The crimping mechanism is also illustrated in FIG. 14. In this embodiment of the present invention, crimping mechanism 56 constitutes a metal ring or collar that tightly encircles sections of the spines 16. For example, the spines 16 may be formed from elongated wire elements (not separately designated) each having a curved hook 56 at both ends. The hooks 56 each have a concave side and a convex side, each side having a smoothly arcuate configuration with a sharp distal tip extending back in a proximal direction. The elongated wire elements are bent, approximately midway along the element to form multiple spines 16. The crimping mechanism 56 holds the spines together below the bend to effectively form a loop or eyelet 52 through which a line element 11, such as a suture thread, may pass to hold the anchors together. As shown in FIGS. 10 and 11, the present invention contemplates that the concave and convex sides of the hooks 56 retain their smoothly arcuate configurations both in a collapsed pre-deployment configuration (FIGS. 1A, 7, 11) and in an opened or expanded deployed configuration (FIGS, 1A, 6, 10 and 14).

Returning to FIG. 6, a line element or thread 11 runs through a proximal loop 38 of anchor 10. The crimping mechanism 34, which acts as a body for the anchors 10, may be formed of a different or similar material as spines 16. Rather than loop 38, the body 34 might be provided with an opening through which line element 11 may traverse.

The anchors 10 are contained within the elongated body 12, which in certain embodiments is configured for holding a plurality of anchors. The anchors 10 are stacked behind one another inside elongated tubular body 12. Anchors 10 are pushed forward by pushing device 14, the distal end thereof is proximate the proximal end of the most proximal anchor.

Thus, as the rearmost anchor is pushed, it in turn pushes the next anchor and so on until all of the anchors are deployed from the distal end of the device 5.

The spines 16 of FIGS. 6 and 7 are dual ended spines 16 being held together by crimping mechanism 34. The suture thread 11 runs through a loop 38 in the distal end of the anchor 10. In one embodiment, the anchor spines are made of a shape memory alloy. The spines might assume a martensitic state when forcibly collapsed, so as to be collapsed and passed through elongated body 12 and a flexible endoscope. The spines assume an austenitic state transforming the anchor into a certain splayed or spread configuration at body temperature when positioned inside a target tissue. The curvature of the curved ends 36 and/or 37 might also be affected by body temperature rendering the ends stiffer and more curved for providing optimal anchoring.

While body temperature is one way to achieve an austenitic state with an anchor made from an SMA, an alternative embodiment might deliver warm fluid to the anchors through fluid port 30 and passageway 15 to induce an austenitic state.

FIG. 7 illustrates a fully retracted or collapsed anchor 10 with dual ended spines 16 held together by crimping mechanism 34. This is generally the configuration in which the multiple anchors would be stored in elongated tubular body 12 of fastening assembly 5 prior to being deployed.

Figure 1A:
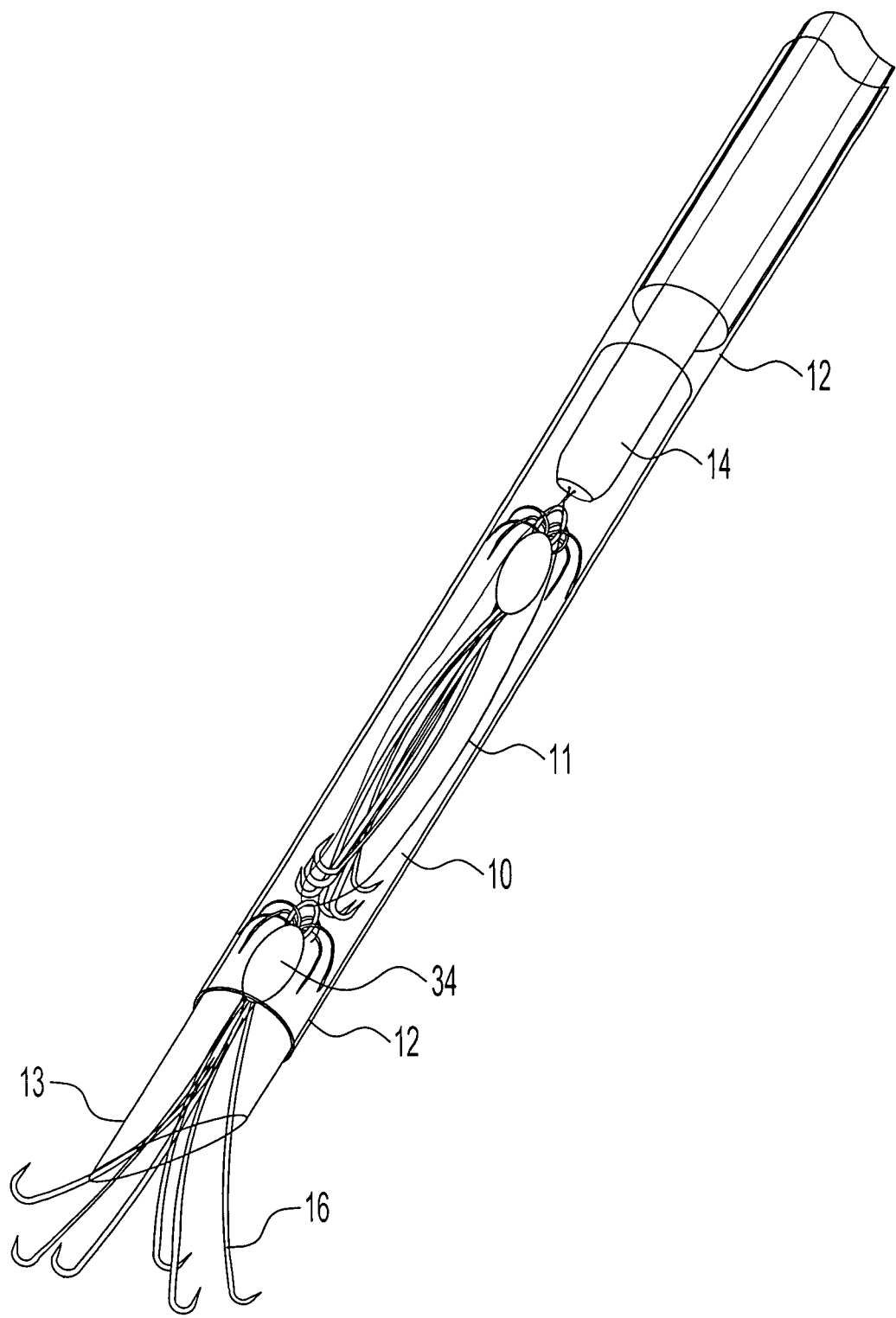
FIG. 1A is a perspective view of the distal end of the embodiment of FIG. 1.
Figure 8:
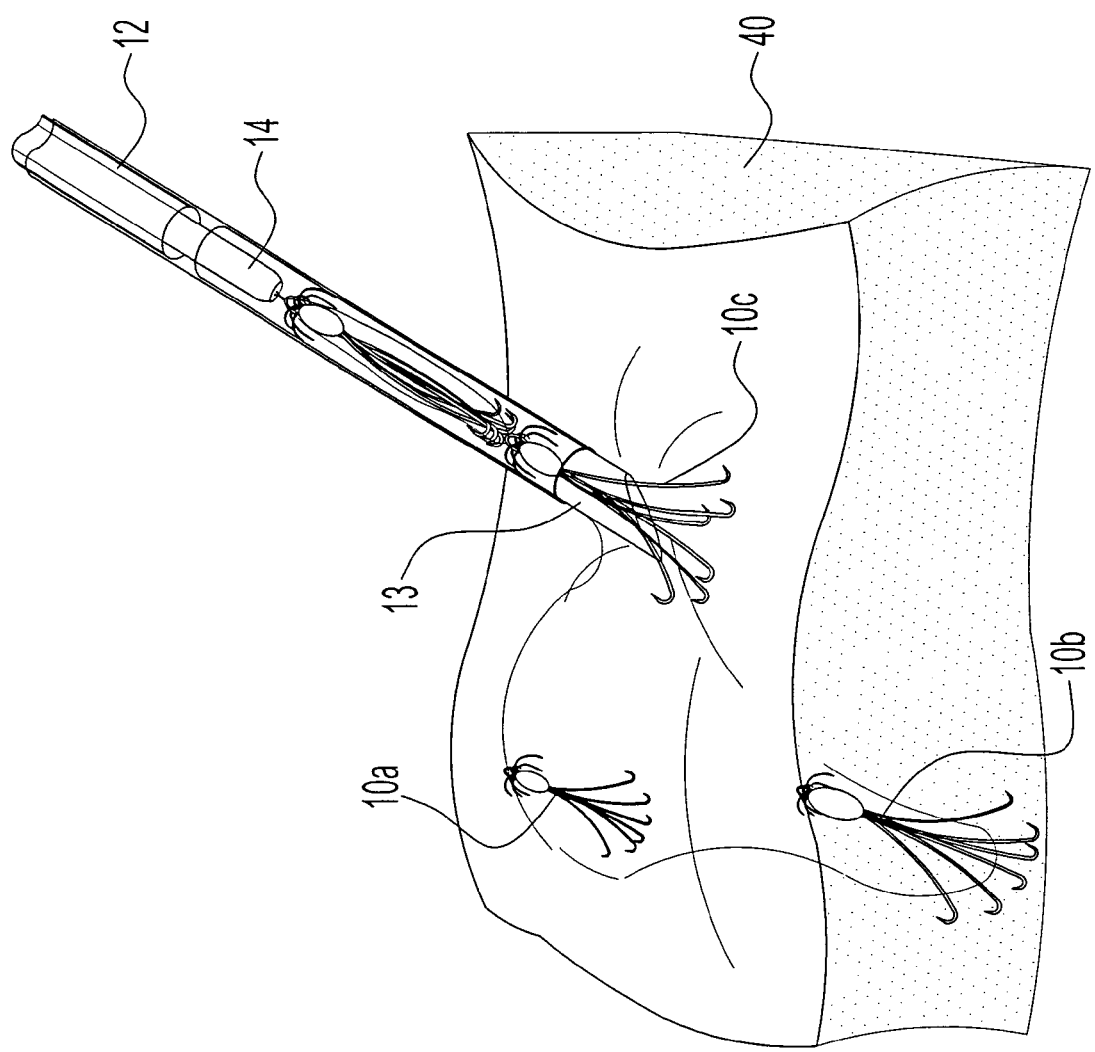
FIG. 8 is a perspective view of the anchors of an embodiment being deployed into tissue in accordance with the present invention.

FIG. 8 illustrates the fastening assembly 5 with a plurality of anchors 10 being deployed into tissue 40 through hollow needle 13 and coupled by a suture thread or other line element. As illustrated, anchors 10a and 10b have been deployed and anchor 10c is being deployed. Anchors 10 emerge from needle 13 being pushed by pushing device 14. The needle may be elongated as shown in FIG. 1A to form an anchor holder within elongated tubular body 12. Alternatively, there may be another anchor holder mechanism employed in tubular body 12, serving to hold the anchors inside tubular body 12 until they are deployed. The anchors 10 are stacked in needle 13 or other anchor holder as shown in FIGS. 1, 1A and 2 so that the anchors will be deployed sequentially, one at a time, with the anchors being pushed by the next sequential anchor or by pushing device 14.

Figure 3:
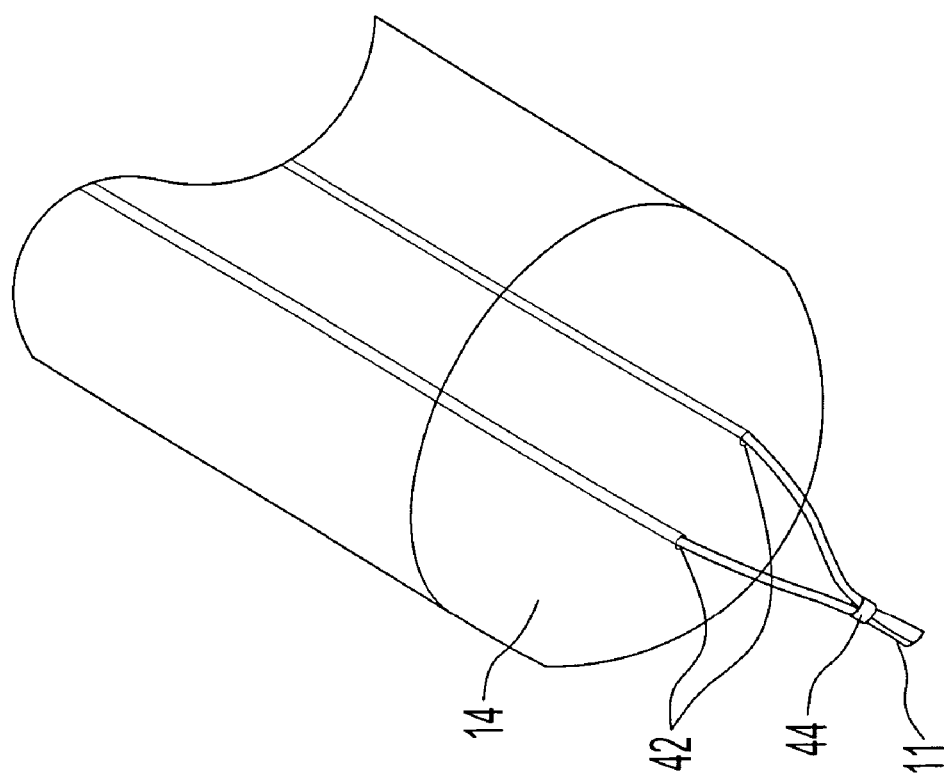
FIG. 3 is a perspective view, cut away, of a pushing device in accordance with an embodiment of the invention.
Figure 9:
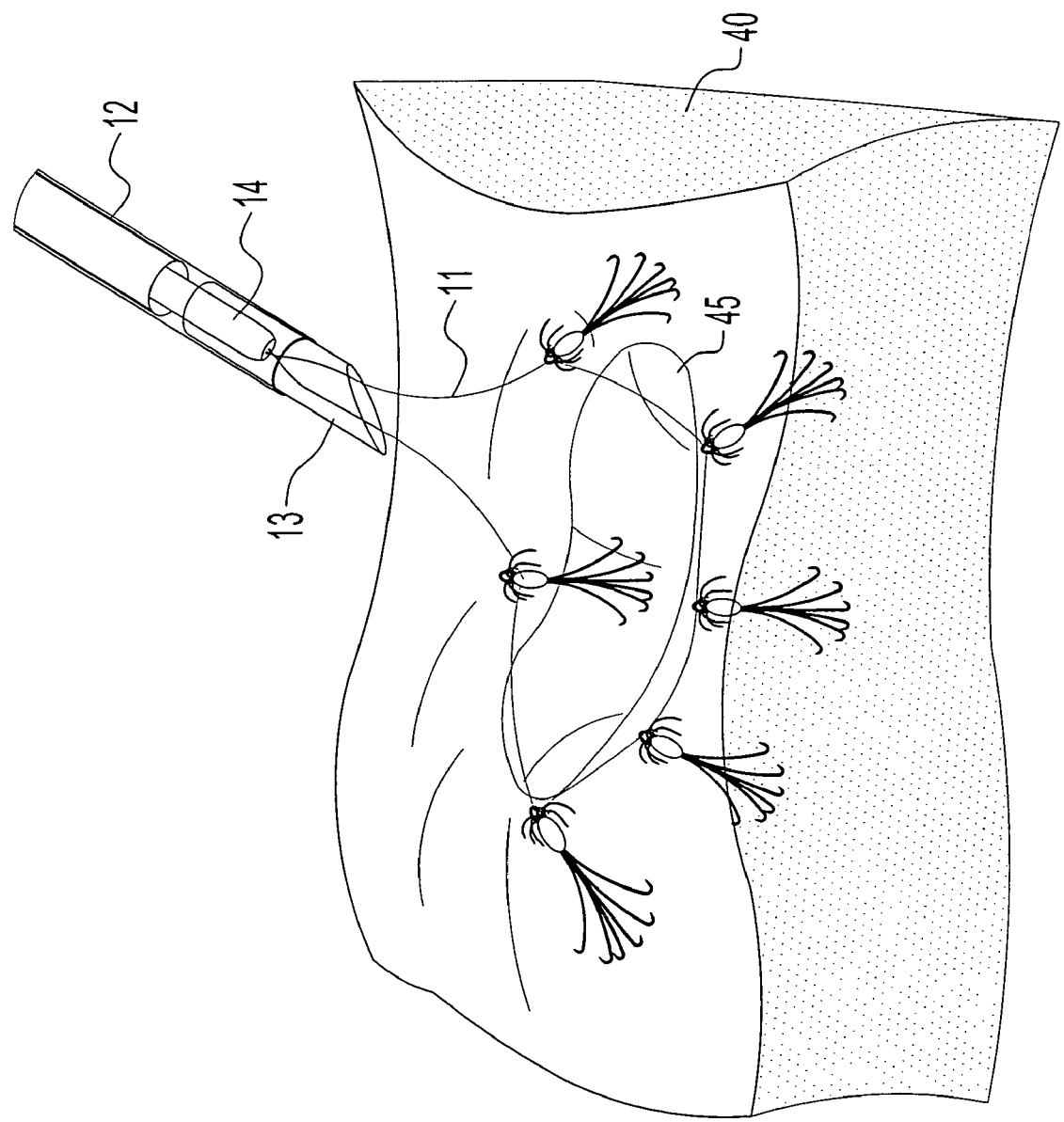
FIG. 9 is a perspective view of the anchors of FIG. 8 deployed in tissue and connected by a line element in the form of a purse string.

FIG. 9 shows anchors 10 deployed in tissue 40 and connected by thread or line element 11, with thread 11 traversing longitudinally through the center of push rod 14. Thread 11 may be a suitable wire or suture. Referring to FIG. 3, thread 11 may be fed through openings 42 in rod 14. The thread may be secured at one or more places along its length with a clip or collar 44.

Anchors 10 are shown positioned in tissue 40 to surround an opening or incision 45 in the tissue so as to close the incision. Thread 11 is flexible and biocompatible, and may be made of a bioabsorbable or non-bioabsorbable material. Furthermore, the thread may come in various thicknesses. Anchors 10 are coupled together with thread 11 in such a fashion as to facilitate cinching or pulling together of the deployed anchors causing a cinching or pleating of the target tissue. Once anchors 10 are positioned in tissue 40 as shown in FIGS. 8 and 9, the thread may be used to cinch the anchors for approximating segments of tissue together. The thread or line element might be continuous or common to couple all anchors together or each anchor may have its own line element, such that when cinching together is desired, all line elements are coupled together.

FIG. 10 is a perspective view of an alternative anchor 50 of the invention in an open configuration. Anchor 50 includes spines 52 that have hooks or curved ends 54 only at the spines' distal ends. The spines are held together by crimping mechanism 56 and suture thread 11 traverses an opening formed in the crimping mechanism. Crimping mechanism 56, which acts as a body for anchor 50, may be formed of a different or similar material as spines 52.

FIG. 11 shows a fully retracted anchor 50 with spines 52 in a collapsed state and held together by crimping mechanism 56.

Figure 12:
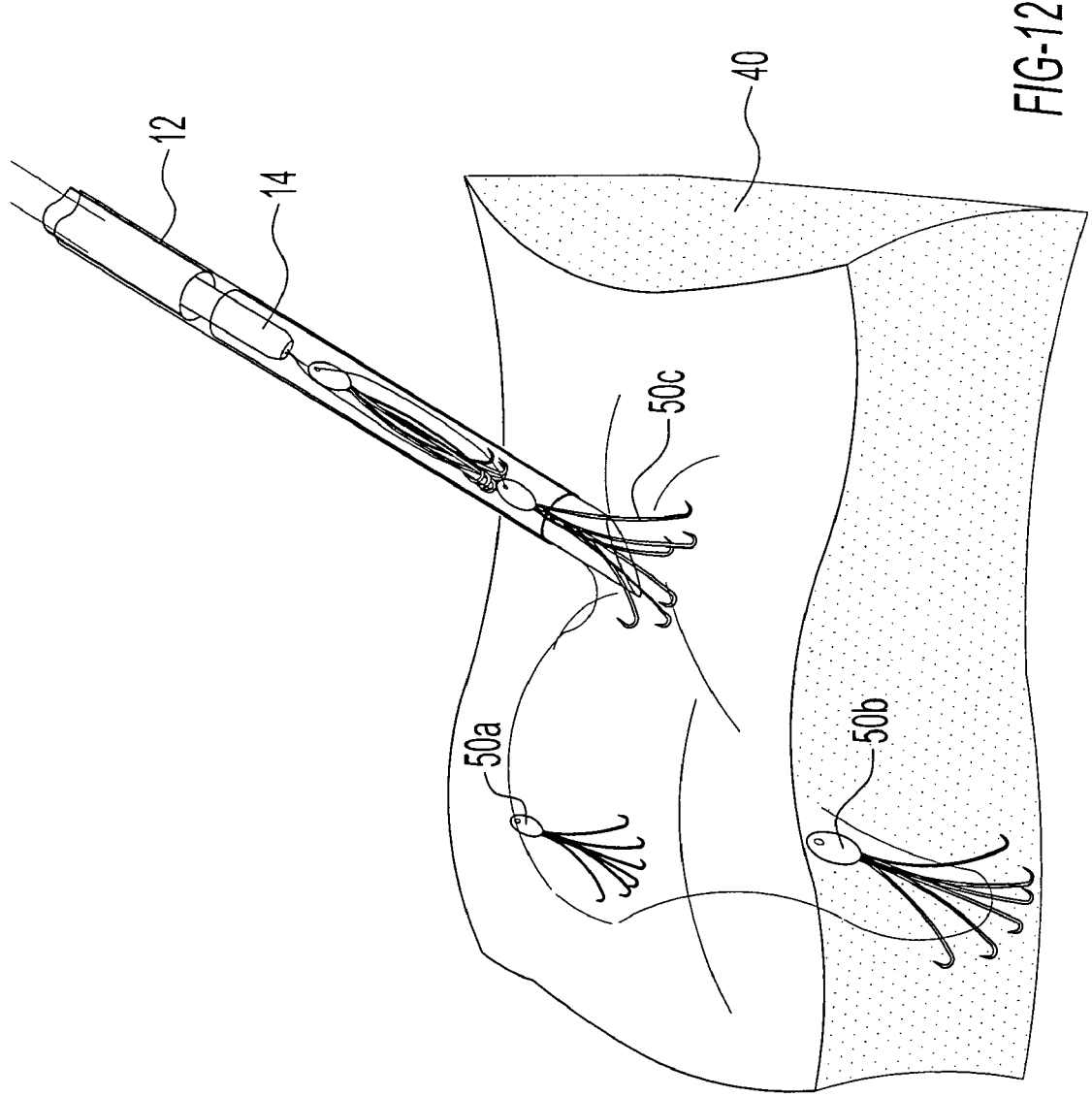
FIG. 12 is a perspective view of anchors being deployed into tissue.

FIG. 12 illustrates device 5 in use in tissue with a plurality of anchors 50 being deployed into tissue 40 through hollow needle 13 and connected by thread 11. For example, anchors 50a and 50b have been deployed and anchor 50c is in the process of being deployed inside tissue 40. Anchors 50 emerge from needle 13 with pushing device 14 pushing anchors 50 contained in elongated body 12. The needle may be elongated as shown in FIG. 1A to form an anchor holder within body 12. If the device is to be used in conjunction with a flexible endoscope, the needle must be 1.5 centimeters or shorter, because the maximal stiff length that can pass through a flexible endoscope cannot be longer than 1.5 centimeters.

Figure 13:
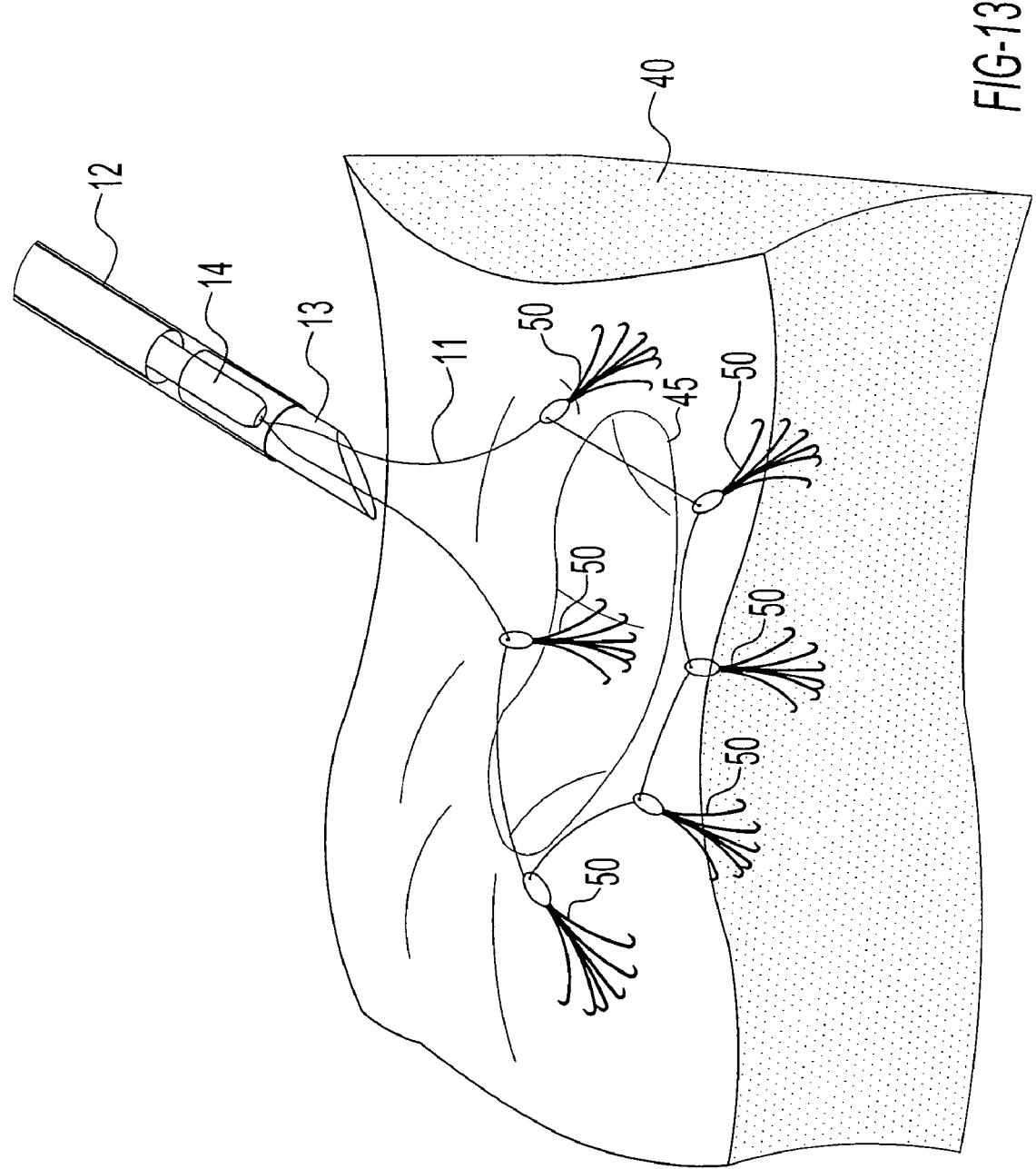
FIG. 13 is a perspective view of the anchors of FIG. 12 deployed in tissue and connected by a line element.

FIG. 13 illustrates anchors 50 deployed in tissue 40 and connected by a line element, such as a suture, thread 11 or wire, with line element or thread 11 running through the center of pushing device 14. Referring again to FIG. 3, thread 11 may be fed through openings 42 in pushing device 14. Thread 11 may be secured at one or more places along its length with a device such as a clip or collar 44.

Using the present invention, certain bariatric procedures might be performed. A flexible endoscope might be inserted through the mouth, and esophagus into the stomach. The cinching, pleating or approximating of tissue using fastening assembly 5 and anchors 10 may be accomplished by pulling on embedded anchors 10 to thereby restrict the volume of the stomach or make for an effectively smaller entryway into the stomach. Alternatively, an anti reflux procedure might be performed. The cinching, pleating, or approximating of tissue using the device by pulling on the coupling suture thread that communicates between the anchors that are embedded below an incompetent gastroesophageal sphincter restricts the opening of the sphincter, thus treating gastroesophageal reflux disease (GERD).

In another aspect of the invention, a method of performing any sphincter tightening or reduction might be deployed. Cinching, pleating or approximating of tissue by pulling anchors that are embedded at or near a sphincter constricts the lax sphincter. Fastening assembly 5 might also be used for suturing, control of hemorrhage or closing a perforation by delivering two or more anchors at opposite sides of a bleeding or perforation site, and cinching the anchors together.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed:

1. A fastening assembly comprising:
   an elongate tubular body provided with a hollow sharp needle tip at one end thereof; and
   one or more expandable anchors, each said anchor comprising at least two elongate wires bent to form an eyelet on one side and a plurality of spines on an opposite side, the bent wires held together, by a crimping mechanism, said spines each comprising a curved hook at a free end thereof, opposite the eyelet of the respective one of said anchors,
   said anchors having a collapsed pre-deployment configuration inside said elongate tubular body, the spines of each said anchor being held closely together in said collapsed pre-deployment configuration,
   said anchors having an expanded deployment configuration outside said elongate tubular body, wherein said spines are splayed open.

2. The fastening assembly in accordance with claim 1, wherein said anchors are made from at least one of metal or plastic.

3. The fastening assembly in accordance with claim 1, wherein said anchors are made at least partially of a spring biased metal.

4. The fastening assembly in accordance with claim 1, wherein said anchors are made at least partially of a shape memory metal.

5. The fastening assembly in accordance with claim 1, wherein said anchors are made at least partially of a temperature-biased shape memory metal.

6. The endoscopic fastening assembly in accordance with claim 1, wherein said crimping mechanism is ring shaped.

7. The fastening assembly in accordance with claim 1, wherein said fastening assembly further comprises a line element coupled to at least one of said anchors.

8. The endoscopic fastening assembly in accordance with claim 7, wherein said line element is provided for an individual one of said anchors.

9. The endoscopic fastening assembly in accordance with claim 7, wherein said line element is provided for coupling together two or more of said anchors.

* * * * *